United States Patent
Lecloux et al.

(10) Patent No.: US 6,962,995 B2
(45) Date of Patent: Nov. 8, 2005

(54) CHARGE TRANSPORT COMPOSITIONS AND ELECTRONIC DEVICES MADE WITH SUCH COMPOSITIONS

(75) Inventors: Daniel David Lecloux, Buellton, CA (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/612,493

(22) Filed: Jul. 2, 2003

(65) Prior Publication Data

US 2004/0068115 A1 Apr. 8, 2004

Related U.S. Application Data

(60) Provisional application No. 60/394,767, filed on Jul. 10, 2002, and provisional application No. 60/458,277, filed on Mar. 28, 2003.

(51) Int. Cl.$^7$ .................... C07D 471/02; C07D 471/00
(52) U.S. Cl. ........................... 546/88; 546/81
(58) Field of Search ............... 546/88, 81; 252/301.26, 252/301.16

(56) References Cited

U.S. PATENT DOCUMENTS

| | | | | |
|---|---|---|---|---|
| 4,853,090 A | * | 8/1989 | Daniel et al. ............ | 205/781.5 |
| 5,077,142 A | | 12/1991 | Sakon et al. | |

FOREIGN PATENT DOCUMENTS

| | | |
|---|---|---|
| EP | 0 341 859 A1 | 11/1989 |
| EP | 0 564 224 A2 | 10/1993 |
| EP | 1 013 740 A2 | 6/2000 |
| EP | 1 097 981 A2 | 5/2001 |
| WO | WO 02/30159 A1 | 4/2002 |
| WO | WO 02/43449 A1 | 5/2002 |

OTHER PUBLICATIONS

Dietrich–Buchecker, Christiane et al., Selective and efficient synthesis of di–, tri– and tetrasubstituted 1,10–phenathrolines, Tetrahedron Letters, 1999, 3395–3396, 40, Elsevier Science Ltd.

Sun, Li–Xian et al., PVC membrane lithium–selective electrodes based on oligomethylene–bridged bis–1,10–phenanthroline derivatives, Analytica Chimica Acta, 1996, 57–64, 329, Elsevier Science B.V.

JP2002352961, Organic Electroluminescent Device, Patent Abstracts of Japan, Dec. 6, 2002, vol. 2003, No. 4, Toray Ind, Inc.

JP2001110572, Field Light Emitting Element, Patent Abstracts of Japan, Apr. 20, 2001, vol. 2000, No. 26, Toray Ind. Inc.

JP2001267080, Light Emission Element, Patent Abstracts of Japan, Sep. 28, 2001, vol. 2000, No. 26, Toray Ind. Inc.

* cited by examiner

Primary Examiner—Charanjit S. Aulakh

(57) ABSTRACT

The present invention relates to charge transport compositions. The invention further relates to electronic devices in which there is at least one active layer comprising such charge transport compositions.

1 Claim, 11 Drawing Sheets

(I)

II(a)

II(b)

I(a)

I(b)

I(c)

I(d)

I(e)

I(f)

I(g)

I(h)

I(i)

III(a)

III(b)

III(c)

III(d)

III(e)

III(f)

III(g)

III(h)

IV(a)

IV(b)

IV(c)

IV(d)

IV(e)

DDPA (Compound F)

DPA (Compound G)

MPMP (Compound A)

TPD (Compound B)

MTDATA (Compound C)

NPB (Compound D)

CBP (Compound E)

CHARGE TRANSPORT COMPOSITIONS AND ELECTRONIC DEVICES MADE WITH SUCH COMPOSITIONS

CROSS REFERENCE TO RELATED APPLICATIONS

This application claims priority from U.S. Provisional Application Ser. No. 60/394767, filed Jul. 10, 2002, and U.S. Provisional Application Ser. No. 60/458277, filed Mar. 28, 2003.

BACKGROUND OF THE INVENTION

1. Field of the Invention

The present invention relates to charge transport compositions. The invention further relates to photoactive electronic devices in which there is at least one active layer comprising such charge transport compositions.

2. Background

In organic photoactive electronic devices, such as light-emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices which use photoactive materials, frequently include one or more charge transport layers, which are positioned between the photoactive (e.g., light-emitting) layer and one of the contact layers. A hole transport layer may be positioned between the photoactive layer and the hole-injecting contact layer, also called the anode. An electron transport layer may be positioned between the photoactive layer and the electron-injecting contact layer, also called the cathode.

There is a continuing need for charge transport materials and anti-quenching materials.

SUMMARY OF THE INVENTION

The present invention is directed to a charge transport composition comprising a phenanthroline derivative having Formula I, shown in FIG. 1, wherein:

$R^1$ and $R^2$ are the same or different at each occurrence and are selected from H, F, Cl, Br, alkyl, heteroalkyl, alkenyl, alkynyl, aryl, heteroaryl, $C_nH_aF_b$, $OC_nH_aF_b$, $C_6H_cF_d$, and $OC_6H_cF_d$;

a, b, c, and d are 0 or an integer such that a+b=2n+1, and c+d=5, n is an integer;

x is 0 or an integer from 1 through 3;

y is 0, 1 or 2;

with the proviso that there is at least one substituent on an aromatic group selected from F, $C_nH_aF_b$, $OC_nH_aF_b$, $C_6H_cF_d$, and $OC_6H_cF_d$.

In another embodiment, the present invention is directed to a charge transport composition having Formula II(a) or Formula II(b), shown in FIGS. 2A and 2B, wherein:

$R^1$, $R^2$, a through d, n, x and y are as defined above;

$R^3$ is the same or different at each occurrence and is selected from a single bond and a group selected from alkylene, heteroalkylene, arylene, heteroarylene, arylenealkylene, and heteroarylenealkylene;

Q is selected from a single bond and a multivalent group;

m is an integer equal to at least 2; and p is 0 or 1.

In another embodiment, the present invention is directed to an electronic device having at least one active layer comprising a material selected from Formulae I, II(a), and II(b), shown in FIGS. 1, 2A, and 2B, respectively, wherein $R^1$ through $R^3$, Q, a through d, m, n, p, x, and y are as defined above, with the proviso that in Formula I there is at least one substituent on an aromatic group selected from F, $C_nH_aF_b$, $OC_nH_aF_b$, $C_6H_cF_d$, and $OC_6H_cF_d$.

As used herein, the term "charge transport composition" is intended to mean material that can receive a charge from an electrode and facilitates movement through the thickness of the material with relatively high efficiency and small loss of charge. Hole transport compositions are capable of receiving a positive charge from an anode and transporting it. Electron transport compositions are capable of receiving a negative charge from a cathode and transporting it. The term "anti-quenching composition" is intended to mean a material which prevents, retards, or diminishes both the transfer of energy and the transfer of an electron to or from the excited state of the photoactive layer to an adjacent layer. The term "photoactive" refers to any material that exhibits electroluminescence, photoluminescence, and/or photosensitivity. The term "HOMO" refers to the highest occupied molecular orbital of a compound. The term "LUMO" refers to the lowest unoccupied molecular orbital of a compound. The term "group" is intended to mean a part of a compound, such as a substituent in an organic compound. The prefix "hetero" indicates that one or more carbon atoms has been replaced with a different atom. The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted. The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment. The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment. The term "alkenyl" is intended to mean a group derived from a hydrocarbon having one or more carbon-carbon double bonds and having one point of attachment, which group may be unsubstituted or substituted. The term "alkynyl" is intended to mean a group derived from a hydrocarbon having one or more carbon-carbon triple bonds and having one point of attachment, which group may be unsubstituted or substituted. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted. The terms "heteroalkenyl", "heteroalkenylene", "heteroalkynyl" and "heteroalkynlene"

are intended to mean analogous groups having one or more heteroatoms. The terms "heteroalkenyl", "heteroalkenylene", "heteroalkynyl" and "heteroalkynlene" are intended to mean analogous groups having one or more heteroatoms. The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted. The term "arylalkylene" is intended to mean a group derived from an alkyl group having an aryl substituent, which group may be further unsubstituted or substituted. The term "heteroarylalkylene" is intended to mean a group derived from an alkyl group having a heteroaryl substituent, which group may be further unsubstituted or substituted. The term "arylene" is intended to mean a group derived from an aromatic hydrocarbon having at least two points of attachment, which group may be unsubstituted or substituted. The term "heteroarylene" is intended to mean a group derived from an aromatic group having at least one heteroatom and having two points of attachment, which group may be unsubstituted or substituted. The term "arylenealkylene" is intended to mean a group having both aryl and alkyl groups and having one point of attachment on an aryl group and one point of attachment on an alkyl group. The term "heteroarylenealkylene" is intended to mean a group having both aryl and alkyl groups and having one point of attachment on an aryl group and one point of attachment on an alkyl group, and in which there is at least one heteroatom. Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. In addition, the IUPAC numbering system is used throughout, where the groups from the Periodic Table are numbered from left to right as 1 through 18 (CRC Handbook of Chemistry and Physics, 81$^{st}$ Edition, 2000).

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE PREFERRED EMBODIMENTS

Figure 1:
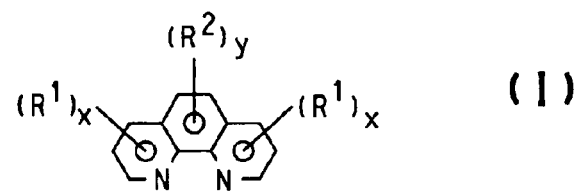
FIG. 1 shows Formula I for a charge transport composition of the invention.

The phenanthroline derivative compounds represented by Formula I, shown in FIG. 1, have particular utility as electron transport compositions and as anti-quenching agents, abbreviated as ET/AQ.

In one embodiment, $R^1$ is selected from phenyl, biphenyl, pyridyl, and bipyridyl, which may further be substituted. Examples of substituents include, but are not limited to, alkyl, heteroalkyl, aryl, heteroaryl, arylalkylene, heteroarylalkylene, F, $C_nH_aF_b$, $OC_nH_aF_b$, $C_6H_cF_d$, and $OC_6H_cF_d$, where a through d and n are as defined above.

In one embodiment, at least one $R^1$ is selected from phenyl and biphenyl, and further substituted with a group selected from F, $C_nH_aF_b$, $OC_nH_aF_b$, $C_6H_cF_d$, and $OC_6H_cF_d$, where a through d and n are as defined above.

In general, n is an integer. In one embodiment, n is an integer from 1 through 20. In one embodiment, n is an integer from 1 through 12.

Examples of suitable ET/AQ compounds of this type include, but are not limited to, those given as Formulae I(a) through I(i) in FIGS. 3A to 3I.

The compositions represented by Formula I can be prepared using standard synthetic organic techniques, as illustrated in the examples. The compounds can be applied as thin films by evaporative techniques or conventional solution processing methods. As used herein, "solution processing" refers to the formation of films from a liquid medium. The liquid medium can be in the form of a solution, a dispersion, an emulsion, or other forms. Typical solution processing techniques include, for example, solution casting, drop casting, curtain casting, spin-coating, screen printing, inkjet printing, gravure printing, and the like.

Figure 2A:
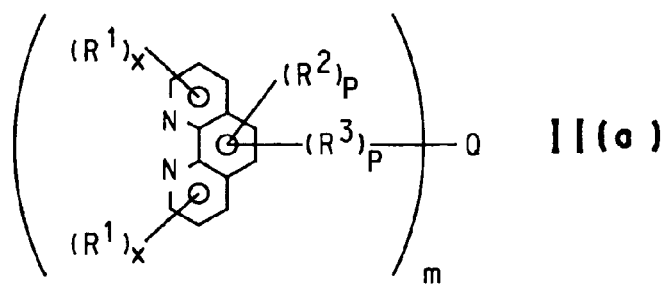
FIGS. 2A and 2B, Formula II(a) and Formula II(b), show a charge transport composition of the invention.
Figure 2B:
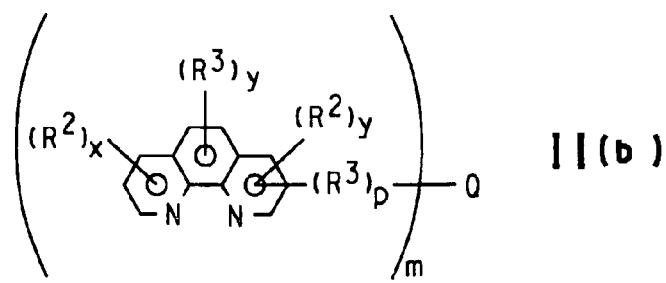

In some cases it is desirable to increase the Tg of the compounds to improve stability, coatability, and other properties. This can be accomplished by linking together two or more of the compounds with a linking group to form compounds having Formula II(a) or Formula II(b), shown in FIGS. 2A and 2B. In these formulae, Q can be a single bond or a multivalent linking group, having two or more points of attachment. The multivalent linking group can be a hydrocarbon group with two or more points of attachment, and can be aliphatic or aromatic. The multivalent linking group can be a heteroalkyl or heteroaromatic group, where the heteroatoms can be, for example, N, O, S, or Si. Examples of multivalent groups, Q, include, but are not limited to, alkylene, alkenylene, and alkynylene groups, and analogous compounds with heteroatoms; single, multiple-ring, and fused-ring aromatics and heteroaromatics; arylamines, such as triarylamines; silanes and siloxanes. Additional examples of suitable linking groups, Q, are given in FIGS. 4A to 4H as Formulae III(a) through III(h). In Formula III(f), any of the carbons may be linked to a charge transport moiety. In Formula III(h), any of the Si atoms can be linked to a charge transport moiety. Heteroatoms such as Ge and Sn can also be used. The linking group can also be —[SiMeR$^1$—SiMeR$^1$]$_n$—, where R$^1$ and n are as defined above.

In general, m is an integer equal to at least 2. The exact number depends on the number of available linking positions on Q and on the geometries of the phenanthroline moiety and Q. In one embodiment, m is an integer from 2 through 10.

In general, n is an integer. In one embodiment, n is an integer from 1 through 20. In one embodiment, n is an integer from 1 through 12.

In one embodiment, R$^1$ is selected from phenyl, biphenyl, pyridyl, and bipyridyl, which may further be substituted. Examples of substituents include, but are not limited to, alkyl, heteroalkyl, aryl, heteroaryl, arylalkylene, heteroarylalkylene, F, $C_nH_aF_b$, $OC_nH_aF_b$, $C_6H_cF_d$, and $OC_6H_cF_d$, where a through d and n are as defined above.

In one embodiment, at least one R$^1$ is selected from phenyl and biphenyl, and further substituted with a group selected from F, $C_nH_aF_b$, $OC_nH_aF_b$, $C_6H_cF_d$, and $OC_6H_cF_d$, where a through d and n are as defined above.

In one embodiment, R$^3$ is selected from a phenylene and a substituted phenylene. Examples of substituents include, but are not limited to, alkyl, heteroalkyl, aryl, heteroaryl, arylalkylene, heteroarylalkylene, F, $C_nH_aF_b$, $OC_nH_aF_b$, $C_6H_cF_d$, and $OC_6H_cF_d$, where a through d and n are as defined above.

In one embodiment, R$^3$ is selected from an alkylene group having from 1 through 20 carbon atoms.

In one embodiment, there is at least one substituent on an aromatic group selected from F, $C_nH_aF_b$, $OC_nH_aF_b$, $C_6H_cF_d$, and $OC_6H_cF_d$.

Figure 6:
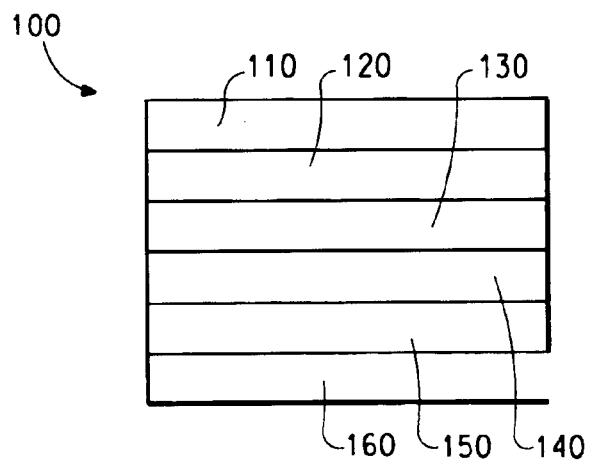
FIG. 6 is a schematic diagram of a light-emitting diode (LED).
Figure 7A:
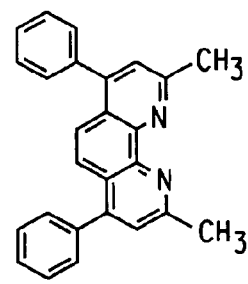
FIGS. 7A–7B formulae for known electron transport compositions.
Figure 7B:
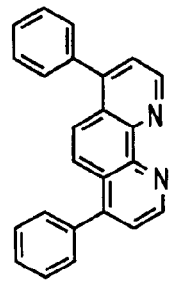

The compositions represented by Formula II(a) and Formula II(b) can be prepared using standard synthetic organic techniques Electronic Device The present invention also relates to an electronic device comprising at least one of the charge transport compositions of the invention positioned between a photoactive layer and one electrode. A typical device structure is shown in FIG. 6. The device 100 has an anode layer 110 and a cathode layer 160. Adjacent to the anode is a layer 120 comprising hole transport material. Adjacent to the cathode is a layer 140 comprising an electron transport and/or anti-quenching material. Between the hole transport layer and the electron transport and/or anti-quenching layer is the photoactive layer 130. As an option, devices frequently use another electron transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The phenanthroline derivative compounds of the invention are particularly useful as the electron transport and/or anti-quenching composition in layer 140, or as electron transport composition in layer 150.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8–10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," *Nature* vol. 357, pp 477–479 (11 Jun. 1992). At least one of the anode and cathode should be at least partially transparent to allow the generated light to be observed.

Examples of hole transport materials which may be used for layer 120 have been summarized, for example, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N', N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, and polyaniline and mixtures thereof. It is also possible to obtain hole transporting polymers by doping hole transporting molecules such as those mentioned above into polymers such as polystyrene and polycarbonate.

Examples of the photoactive layer 130 include all known electroluminescent materials. Organometallic electroluminescent compounds are preferred. The most preferred compounds include cyclometalated iridium and platinum electroluminescent compounds and mixtures thereof. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications U.S. 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1–3), 379–383, and Campbell et al., in Phys. Rev. B, Vol. 65 085210. Examples of a few suitable iridium complexes are given in FIG. 5, as Formulae IV(a) through IV(e). Analogous tetradentate platinum complexes can also be used. These electroluminescent complexes can be used alone, or doped into charge-carrying hosts, as noted above. The compositions of the present invention, in addition to being useful in the electron transport and/or anti-quenching layer 140, may also act as a charge carrying host for the emissive dopant in the photoactive layer 130.

Examples of additional electron transport materials which can be used in layer 150 include metal chelated oxinoid compounds, such as tris(8-hydroxyquinolato)aluminum ($Alq_3$); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, thee electron transport layers 140 and 150, and cathode layer 160, may be surface treated to increase charge carrier transport efficiency. The choice of materials for each of the component layers is preferably determined by balancing the goals of providing a device with high device efficiency with device operational lifetime.

It is understood that each functional layer may be made up of more than one layer.

The device can be prepared by a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique, including but not limited to spin-coating, dip-coating, and roll-to-roll techniques. In general, the different layers will have the following range of thicknesses: anode 110, 500–5000 Å, preferably 1000–2000 Å; hole transport layer 120, 50–2000 Å, preferably 200–1000 Å; photoactive layer 130, 10–2000 Å, preferably 100–1000 Å; electron transport layer 140 and 150, 50–2000 Å, preferably 100–1000 Å; cathode 160, 200–10000 Å, preferably 300–5000Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

The phenanthroline derivative compounds of the invention may be useful in applications other than OLEDs. For example, these compositions may be used in photovoltaic devices for solar energy conversion. They may also be used in field effect transistor for smart card and thin film transistor (TFT) display driver applications.

EXAMPLES

The following examples illustrate certain features and advantages of the present invention. They are intended to be illustrative of the invention, but not limiting. All percentages are by weight, unless otherwise indicated.

Examples 1–5

These examples illustrate the preparation of phenanthroline derivative charge transport compositions having fluorine substitution.

Example 1

This example illustrates the preparation of Compound I(c) in FIG. 3.

A mixture of 2,9-diiodo-1,10-phenanthroline (900 mg, 2.08 mmol, prepared according to: Toyota et al. *Tetrahedron Letters* 1998, 39, 2697–2700), 3-trifluoromethylbenzeneboronic acid (989 mg, 5.20 mmol, Aldrich Chemical Company, Milwaukee, Wis.), tetrakistriphenylphosphine palladium (481 mg, 0.416 mmol, Aldrich Chemical Company), and sodium carbonate (882 mg, 8.32 mmol) were allowed to reflux in water (20 mL)/toluene (50 mL) for 15 h under nitrogen. Then the organic layer was separated, and the aqueous layer extracted with 3×25 mL of chloroform. The organic layers were combined, dried with sodium sulfate, and evaporated to dryness. Purification was accomplished by silica gel flash chromatography with hexanes/dichloromethane (1:1, v:v) as the eluent (product $R_f$=0.25), to afford the desired product, >95% pure by $^1H$ NMR, as a pale yellow solid (560 mg, 57%). $^1H$ NMR ($CDCl_3$, 300 MHz, 296 K): δ8.81 (s, 2H), 8.63 (d, 2H, J=7.5 Hz), 8.36 (d, 2H, J=8.4 Hz), 8.19 (d, 2H, J=8.41 Hz), 7.84 (s, 2H), 7.68–7.77 (m, 6H) ppm. $^{19}F$ NMR ($CDCl_3$, 282 MHz, 296 K) δ-63.25 ppm.

Compounds I(a), I(g), I(h) and I(i) were made using an analogous procedure.

Example 2

Figure 3A:
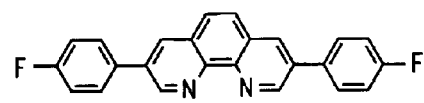
FIGS. 3A–3I, Formulae I(a) through I(i), show a charge transport composition of the invention.
Figure 3B:
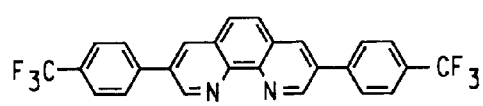
Figure 3C:
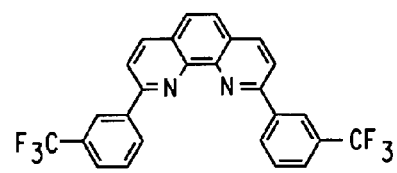

This example illustrates the preparation of Compound I(b) in FIG. 3B.

The same procedure was used as in EXAMPLE 1, with 3,8-dibromo-1,10-phenanthroline (1.5 g, 4.4 mmol, prepared according to: Saitoh et al. *Canadian Journal of Chemistry* 1997, 75, 1336–1339.), 4-trifluoromethylbenzeneboronic acid (2.11 g, 11.1 mmol, Lancaster Chemical Company, Windham, N.H.), tetrakistriphenylphosphine palladium (513 mg, 0.444 mmol), and sodium carbonate (1.41 g, 13.3 mmol), water (20 mL), and toluene (100 mL). Purification was achieved via silica gel flash chromatography (dichloromethane/methanol, 9:1, v:v), and then by washing the product with cold methanol, to afford a white solid (520 mg, 25%)>95% pure by $^1H$ NMR. $^1H$ NMR ($CDCl_3$, 300 MHz, 296 K): δ9.46 (d, 2 H, J=2.3 Hz), 8.45 (d, 2H, 2.3 Hz), 7.94 (s, 2H), 7.91 (d, 4H, J=8.3 Hz), 7.82 (d, 4H, J=8.4 Hz) ppm. $^{19}F$ NMR (CDCl3, 282 MHz, 296 K) δ-63.12 ppm.

Example 3

Figure 3D:
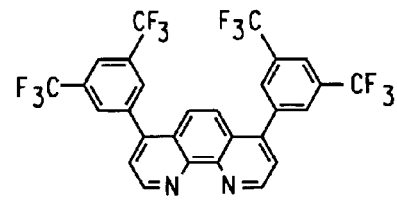
Figure 3E:
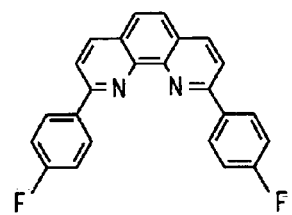

This example illustrates the preparation of Compound I(e) in FIG. 3E.

2,9-Diiodo-1,10-phenanthroline (1.00 g, 2.31 mmol), 4-fluorobenzeneboronic acid (972 mg, 6.96 mmol), bis(diphenylphosphino)butane (92 mg, 0.23 mmol, Aldrich), palladium acetate (52 mg, 0.23 mmol, Aldrich), and potassium fluoride (810 mg, 13.9 mmol, Aldrich) were allowed to reflux in anhydrous dioxane (100 mL) for 15 h, after which time the dioxane was removed under reduced pressure, and the crude residue was subjected to an aqueous work-up as for Example 1. Purification was achieved via silica gel flash chromatography (dichloromethane, 100% product $R_f$=0.57), to afford a pale yellow solid (567 mg, 67%), >95% pure by $^1$H NMR. $^1$H NMR (CDCl$_3$, 300 MHz, 296 K): δ8.43 (dd, 4 H, J$_{HH}$=10.4 Hz, J$_{HF}$=5.5 Hz), 8.28 (d, 2H, J=8.4Hz), 7.77 (s, 2H), 7.26 (dd, 4H, J$_{HH}$=9.9 Hz, J$_{HF}$=5.9 Hz) ppm. $^{19}$F NMR (CDCl3, 282 MHz, 296 K) δ-113.0 ppm.

Example 4

This example illustrates the preparation of Compound I(d) in FIG. 3D.

The same procedure was used as in Examples 20 and 21, using 4,7-dichloro-1,10-phenanthroline (300 mg, 1.20 mmol, prepared according to: *J. Heterocyclic Chemistry* 1983, 20, 681–6), 3,5-bis(trifluoromethyl)benzeneboronic acid (0.930 mg, 3.60 mmol, Aldrich), bis(diphenylphosphino)butane (154 mg, 0.361 mmol), palladium acetate (81 mg, 0.361 mmol), sodium carbonate (0.510 mg, 9.62 mmol), water (5 mL), and toluene (30 mL), to afford the desired product as a white solid (410 mg, 56%). $^1$H NMR (CDCl$_3$, 300 MHz, 296 K): δ9.35 (d, 2H, J=4.49 Hz), 8.06 (s, 2H), 8.00 (s, 4H), 7.73 (2H, s), 7.66 (d, 2H, J=4.52 Hz) ppm. $^{19}$F NMR (CDCl$_3$, 282 MHz, 296 K) δ-63.32 ppm.

Example 5

Figure 3F:
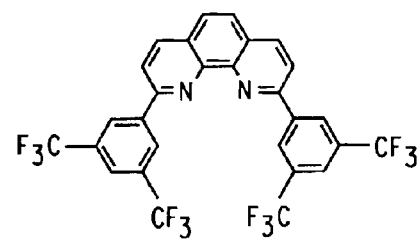
Figure 3G:
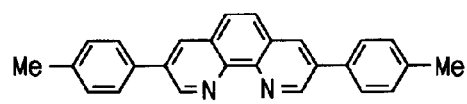
Figure 3H:
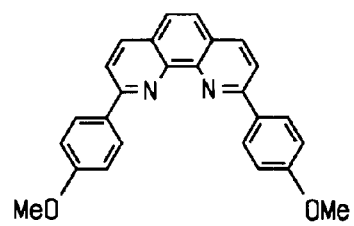
Figure 3I:
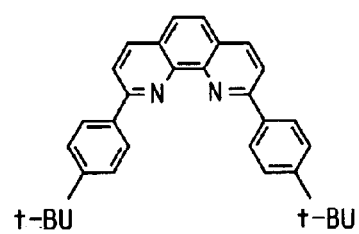
Figure 4A:
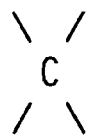
FIGS. 4A–4H, Formulae III(a) through III(h), show a multidentate linking group.
Figure 4B:
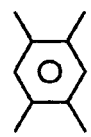
Figure 4C:
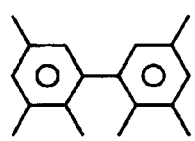
Figure 4D:
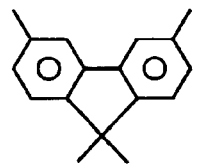
Figure 4E:
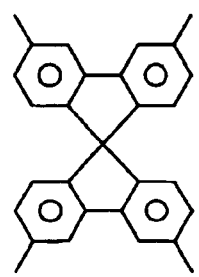
Figure 4F:
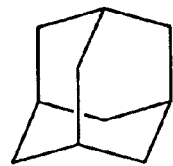
Figure 4G:
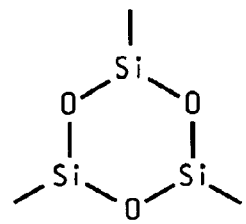
Figure 4H:
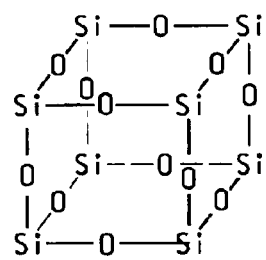

This example illustrates the preparation of Compound I(f) in FIG. 3F.

The same procedure was used as in EXAMPLE 3, using 2,9-dichloro-phenanthroline (1.0 g, 4.01 mmol, prepared according to: Yamada et al. *Bulletin of the Chemical Society of Japan* 1990, 63, 2710–12), 3,5-bistrifluoromethylbenzene-boronic acid (2.59 g, 10.0 mmol), bis(diphenylphosphino)butane (171 mg, 0.401 mmol), palladium acetate (90 mg, 0.401 mmol), and potassium fluoride (1.40 g, 24.1 mmol), and anhydrous dioxane (100 mL). The product was purified by washing the crude material with diethyl ether, to afford the desired product as a white solid (345 mg, 14%). $^1$H NMR (CDCl$_3$, 300 MHz, 296 K): δ8.92 (d, 4H, J$_{HF}$=1.46 Hz), 8.45 (d, 2H, J=8.3 Hz), 8.25 (d, 2H, J=8.5 Hz), 8.02 (s, 2H), 7.91 (s, 2H) ppm. $^{19}$F NMR (CDCl$_3$, 282 MHz, 296 K) δ-63.50 ppm.

The properties of the electron transport and/or anti-quenching compositions are summarized in Table 1 below.

| Compounds | Absorption onset (nm), E1–E5 | Absorption maximum (nm) | E½ vs SCE (volt), | LUMO vs vacuum (eV), E1 |
|---|---|---|---|---|
| Compound I(b) | 382 | 318 | –1.56 | –3.28 |
| Compound I(a) | 376 | 320 | –1.77 | –3.07 |
| Compound I(c) | 368 | 342 | –1.68 | –3.16 |
| Compound I(d) | 362 | 310 | –1.54 | –3.3 |
| Compound I(e) | 372 | 342 | –1.8 | –3.04 |
| Compound I(f) | 370 | 342 | –1.52 | –3.32 |
| Comp. F DDPA | 368 | 310 | –1.85 | –2.99 |
| Comp. G DPA | 366 | 316 | –1.95 | –2.89 |

Example 6

Figure 5A:
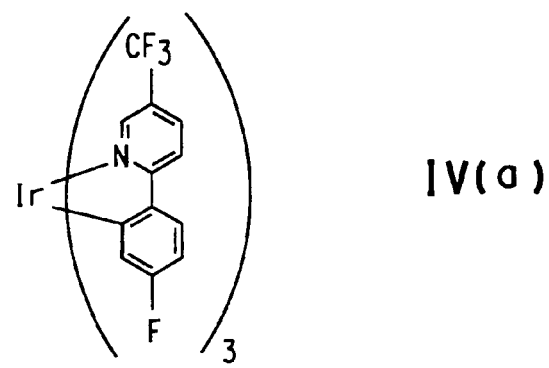
FIGS. 5A–5E Formulae IV(a) through IV(e), show electroluminescent iridium complexes.
Figure 5B:
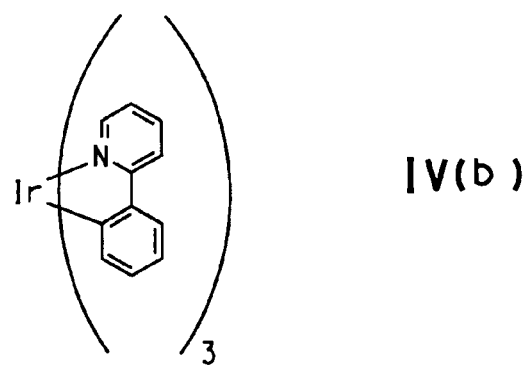
Figure 5C:
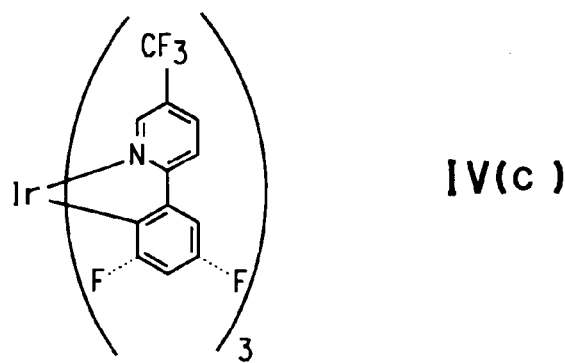
Figure 5D:
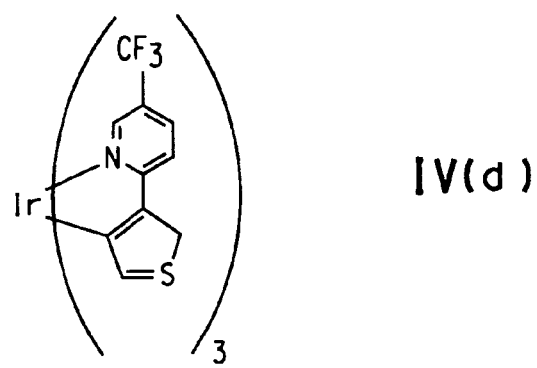
Figure 5E:
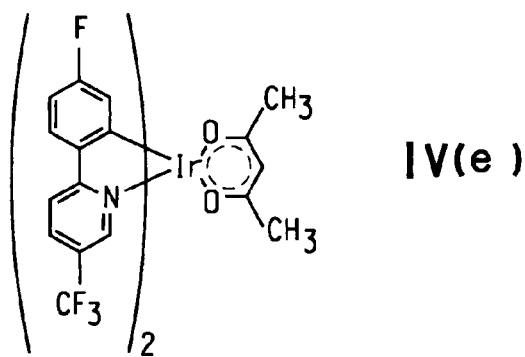

This example illustrates the preparation of an iridium electroluminescent complex, shown as Formula IV(a) in FIG. 5A.

Phenylpyridine ligand, 2-(4-fluorophenyl)-5-trifluoromethylpyridine

The general procedure used was described in O. Lohse, P. Thevenin, E. Waldvogel *Synlett*, 1999, 45–48. A mixture of 200 ml of degassed water, 20 g of potassium carbonate, 150 ml of 1,2-dimethoxyethane, 0.5 g of Pd(PPh$_3$)$_4$, 0.05 mol of 2-chloro-5-trifluoromethylpyridine and 0.05 mol of 4-fluorophenylboronic acid was refluxed (80–90° C.) for 16–30 h. The resulting reaction mixture was diluted with 300 ml of water and extracted with CH$_2$Cl$_2$ (2×100 ml). The combined organic layers were dried over MgSO$_4$, and the solvent removed by vacuum. The liquid products were purified by fractional vacuum distillation. The solid materials were recrystallized from hexane. The typical purity of isolated materials was >98%.

Iridium Complex:

A mixture of IrCl$_3$.nH$_2$O (54% Ir; 508 mg), 2-(4-fluorophenyl)-5-trifluoromethylpyridine, from above (2.20 g), AgOCOCF$_3$ (1.01 g), and water (1 mL) was vigorously stirred under a flow of N$_2$ as the temperature was slowly (30 min) brought up to 185° C. (oil bath). After 2 hours at 185–190° C. the mixture solidified. The mixture was cooled down to room temperature. The solids were extracted with dichloromethane until the extracts decolorized. The combined dichloromethane solutions were filtered through a short silica column and evaporated. After methanol (50 mL) was added to the residue the flask was kept at –10° C. overnight. The yellow precipitate of the tris-cyclometalated complex, compound IVa in FIG. 5, was separated, washed with methanol, and dried under vacuum. Yield: 1.07 g (82%). X-Ray quality crystals of the complex were obtained by slowly cooling its warm solution in 1,2-dichloroethane.

Example 7

This example illustrates the formation of OLEDs using the charge transport compositions of the invention.

Thin film OLED devices including a hole transport layer (HT layer), electroluminescent layer (EL layer) and at least one electron transport and/or anti-quenching layer (ET/AQ layer) were fabricated by the thermal evaporation technique. An Edward Auto 306 evaporator with oil diffusion pump was used. The base vacuum for all of the thin film deposition was in the range of 10$^{-6}$ torr. The deposition chamber was capable of depositing five different films without the need to break up the vacuum.

Patterned indium tin oxide (ITO) coated glass substrates from Thin Film Devices, Inc were used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor for ~3 hours.

The cleaned, patterned ITO substrate was then loaded into the vacuum chamber and the chamber was pumped down to 10$^{-6}$ torr. The substrate was then further cleaned using an oxygen plasma for about 5–10 minutes. After cleaning, multiple layers of thin films were then deposited sequentially onto the substrate by thermal evaporation. Finally, patterned metal electrodes of Al or LiF and Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

Table 2 summarizes the devices made with the phenanthroline derivative ET/AQ compositions of the invention. In all cases the anode was ITO, as discussed above, the hole transport layer was MPMP, shown in FIG. 9, and the emitting layer was the iridium complex from EXAMPLE 6, having the thicknesses indicated. When present, electron transport layer 150 was tris(8-hydroxyquinolato)aluminum (III), Alq, having the thicknesses given. The cathode was a layer of Al or a dual layer of LiF/Al, with the thicknesses given.

TABLE 2

Devices

| Sample | HT (Å) | EL, Å | ET/AQ, Å | ET, Å | Cathode, Å |
|---|---|---|---|---|---|
| Comparative F | 507 | 407 | Comp. F 408 | | Al 721 |
| Comparative G | 507 | 405 | Comp. G 407 | | Al 732 |
| 2-1 | 505 | 406 | I(a) 450 | | Al 717 |
| 2-2 | 506 | 430 | I(b) 405 | | Al 736 |
| 2-3 | 515 | 407 | I(c) 409 | | Al 728 |
| 2-4 | 516 | 419 | I(d) 406 | | Al 717 |
| 2-5 | 505 | 415 | I(e) 432 | | Al 740 |
| 2-6 | 514 | 402 | I(f) 431 | | Al 738 |
| 2-7 | 515 | 407 | I(g) 409 | | Al 728 |

Figure 8:
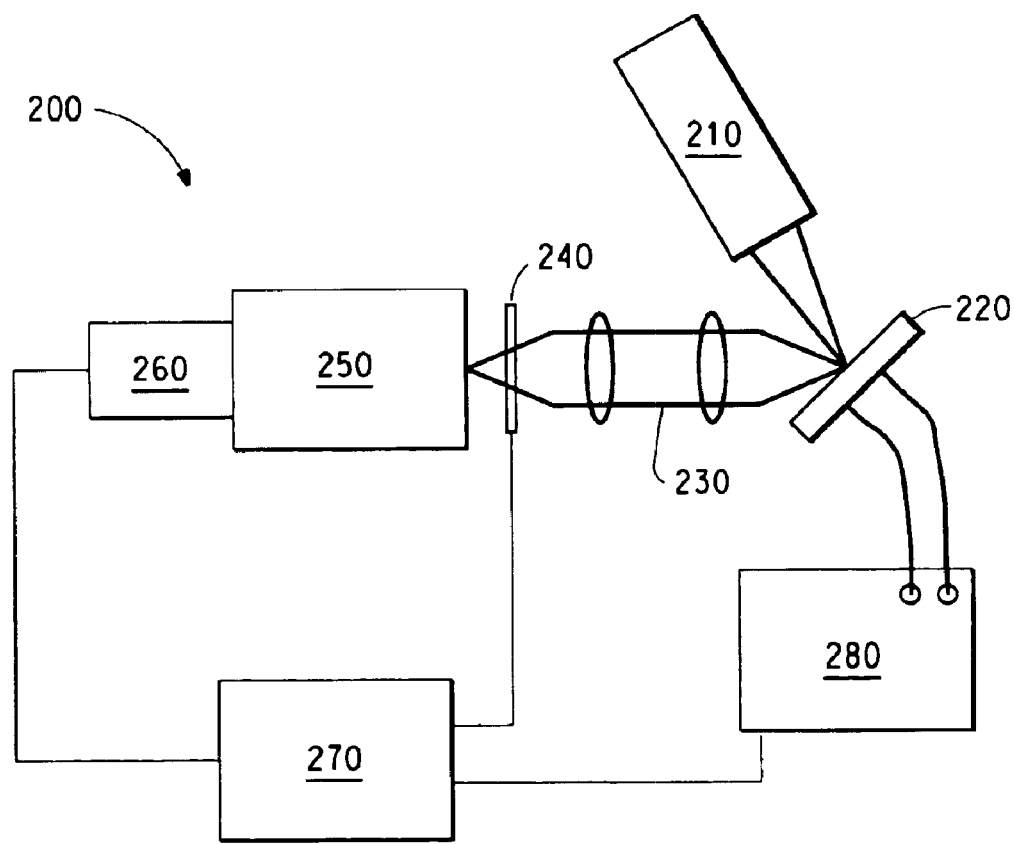
FIG. 8 is a schematic diagram of a testing device for an LED.
Figure 9A:
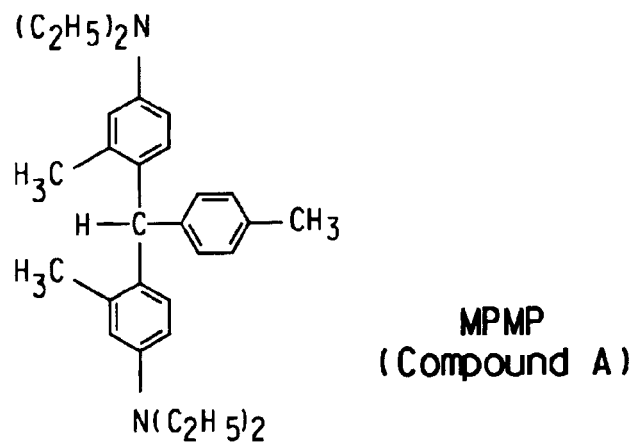
FIG. 9 is an illustration of the formula for MPMP.
Figure 9B:
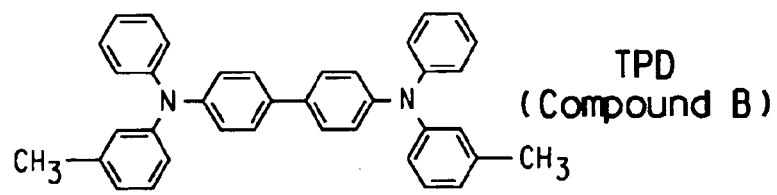
Figure 9C:
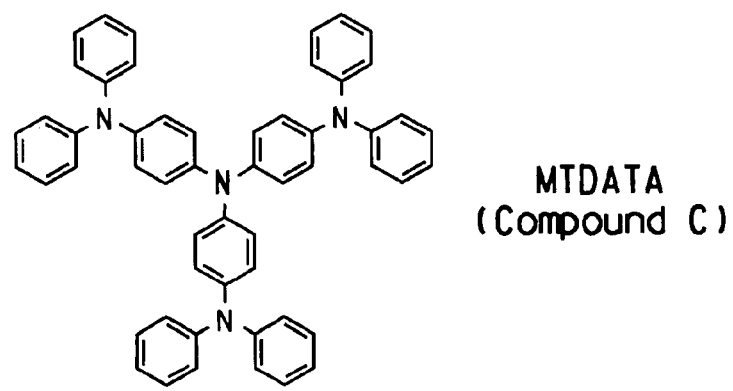
Figure 9D:
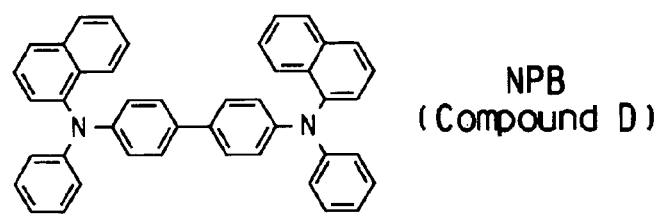
Figure 9E:
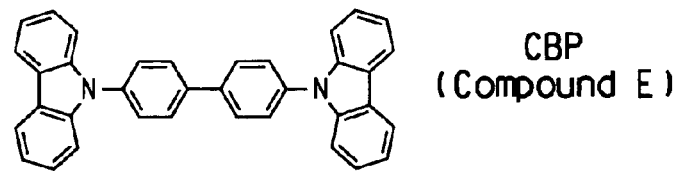

The OLED samples were characterized by measuring their (1) current-voltage (I-V) curves, (2) electroluminescence radiance versus 5 voltage, and (3) electroluminescence spectra versus voltage. The apparatus used, 200, is shown in FIG. 8. The I-V curves of an OLED sample, 220, were measured with a Keithley Source-Measurement Unit Model 237, 280. The electroluminescence radiance (in the unit of cd/m$^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in cd/A.

The results for devices using the phenanthroline derivative ET/AQ compositions of the invention are given in Table 3 below:

TABLE 3

Electroluminescent Properties of Devices

| Sample | Peak Radiance, cd/m2 | Efficiency at Peak Radiance cd/A | Peak efficiency, cd/A |
|---|---|---|---|
| Comp. F | 3000 at 22 V | 10 | 14 |
| Comp. G | 4500 at 19 V | 10 | 20 |
| 2-1 | 4000 at 19 V | 8.5 | 9.5 |
| 2-2 | 3500 at 19 V | 6 | 17 |

TABLE 3-continued

Electroluminescent Properties of Devices

| Sample | Peak Radiance, cd/m2 | Efficiency at Peak Radiance cd/A | Peak efficiency, cd/A |
|---|---|---|---|
| 2-3 | 1200 ± 300 at 24 V | 2 | 6 |
| 2-4 | 2200 at 25 V | | 16 |
| 2-5 | 1000 at 23 V | | 6 |
| 2-6 | 900 at 27 V | | 8.5 |
| 2-7 | 1400 at 24 V | | 6 |

What is claimed is:

1. A phenanthroline derivative selected from Formulae I(b) through I(d) and I(f)

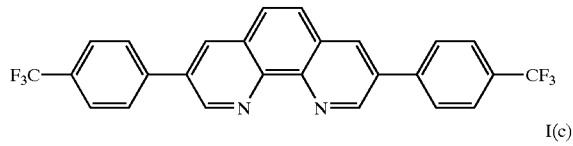

I(b)

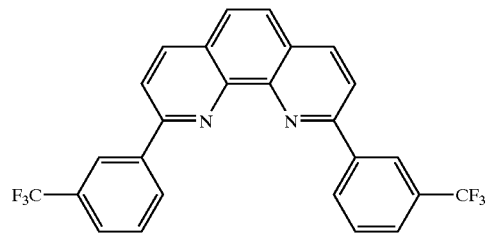

I(c)

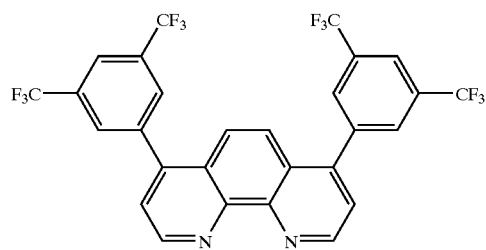

I(d)

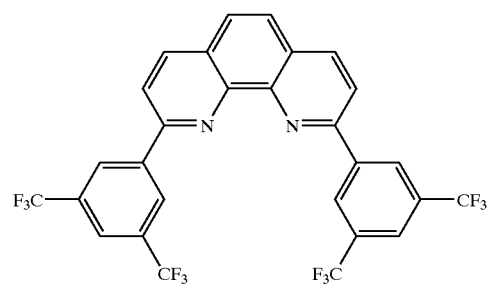

I(f)

* * * * *